United States Patent [19]

Allender

[11] 4,030,028

[45] June 14, 1977

[54] METHOD OF AND APPARATUS FOR DETECTING CONDUCTIVE PARTICLES IN AN OIL FLOW SYSTEM

[76] Inventor: David G. Allender, 23A - 12th Ave., San Mateo, Calif. 94402

[22] Filed: Aug. 13, 1975

[21] Appl. No.: 604,307

[52] U.S. Cl. .................. 324/65 R; 200/61.09; 200/185; 340/236; 340/270
[51] Int. Cl.² ..................... G01R 27/02
[58] Field of Search .......... 324/65 R, 65 P; 340/236, 270; 200/61.09, 185

[56] References Cited

UNITED STATES PATENTS

| | | | |
|---|---|---|---|
| 2,252,222 | 8/1941 | VanOs | 340/270 |
| 2,349,992 | 5/1944 | Schrader | 324/65 R |
| 2,429,920 | 10/1947 | Bourne, Jr. | 200/61.09 X |
| 2,735,907 | 2/1956 | Inman | 324/65 R X |
| 2,937,524 | 5/1960 | Gregor | 324/65 R X |
| 3,193,815 | 7/1965 | Prestel | 340/270 X |
| 3,422,417 | 1/1969 | Lowe | 340/270 |
| 3,696,360 | 10/1972 | Gajewski | 324/65 R X |
| 3,724,474 | 4/1973 | DeVale | 324/65 R X |

*Primary Examiner*—Stanley T. Krawczewicz
*Attorney, Agent, or Firm*—Phillips, Moore, Weissenberger, Lempio & Majestic

[57] ABSTRACT

A method and apparatus for sensing the presence and quantity of conductive particles in an oil flow system is disclosed which method and apparatus is based on a novel sensor element comprising a planar array of a plurality of electrically conductive surfaces interconnected with a plurality of series connected resistor elements. Electronic circuitry for use in combination with the sensor element is described. Preferred embodiments of the sensor element and preferred combinations of sensor element and electronic circuitry are disclosed.

20 Claims, 6 Drawing Figures

U.S. Patent June 14, 1977 Sheet 1 of 2 4,030,028
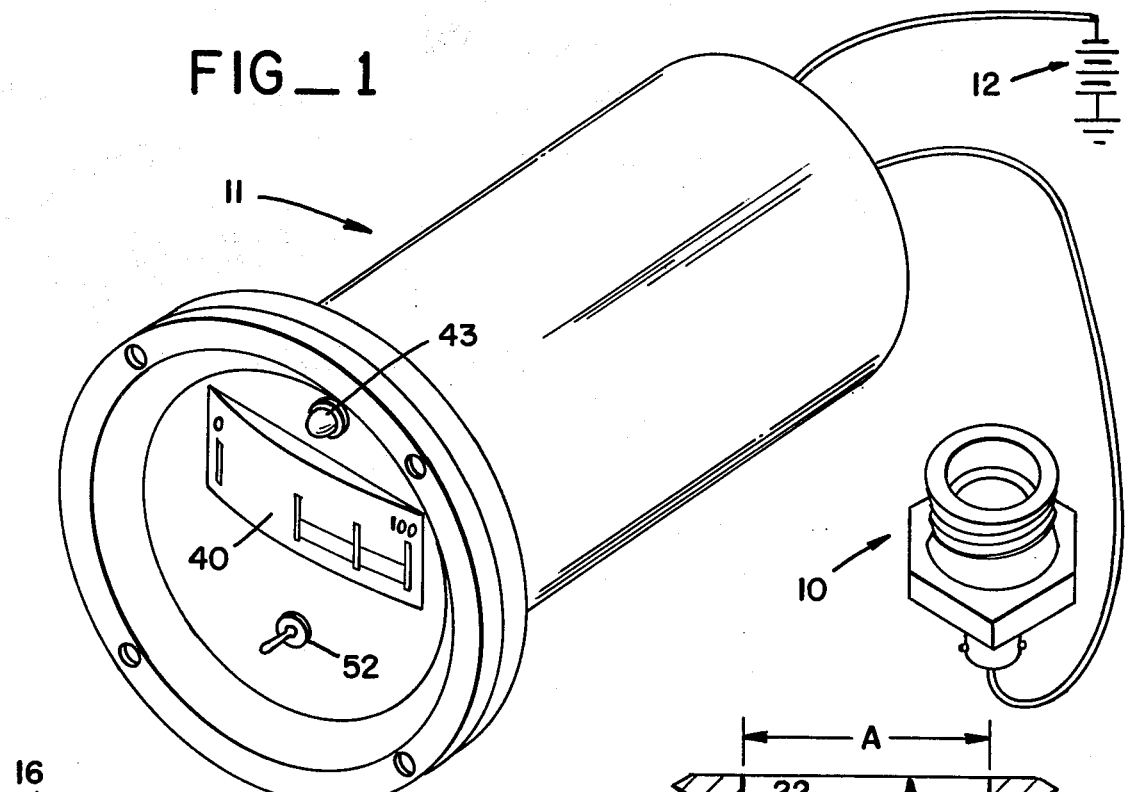
FIG_1
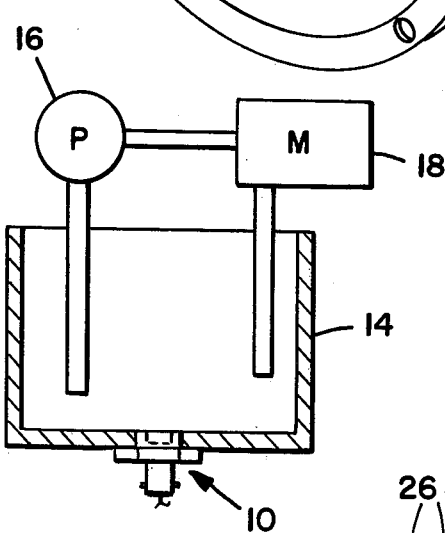
FIG_2
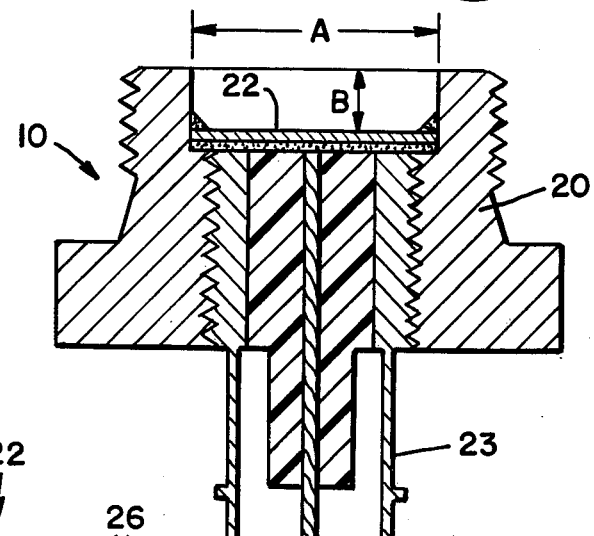
FIG_3
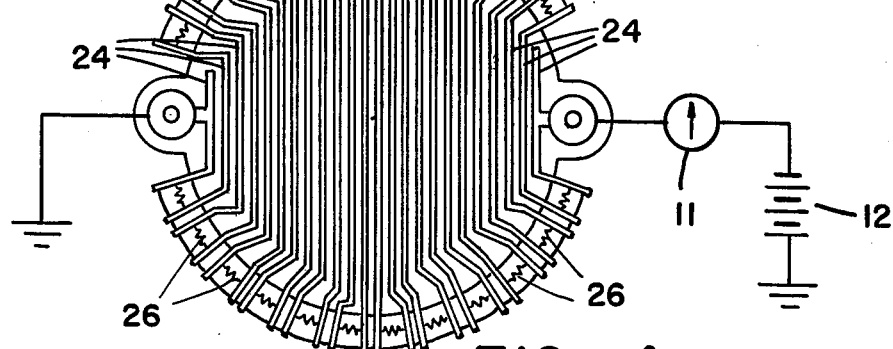
FIG_4

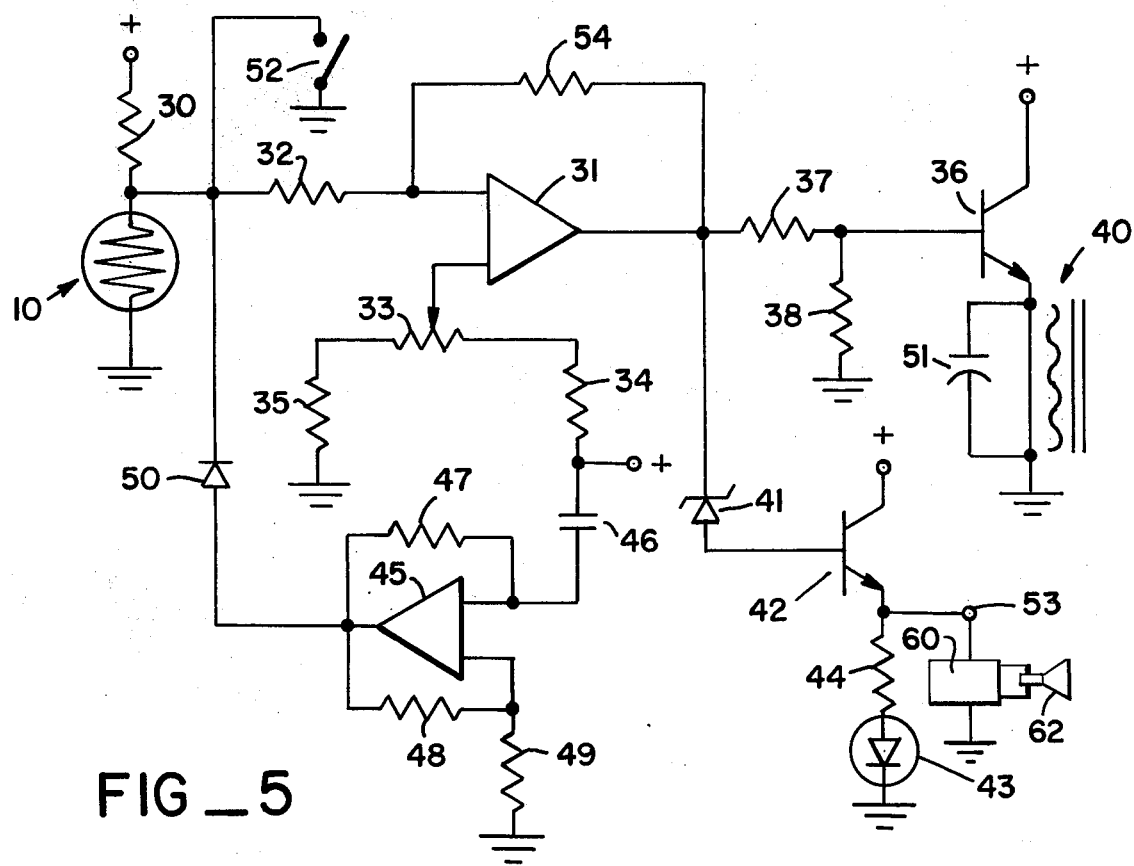
FIG_5
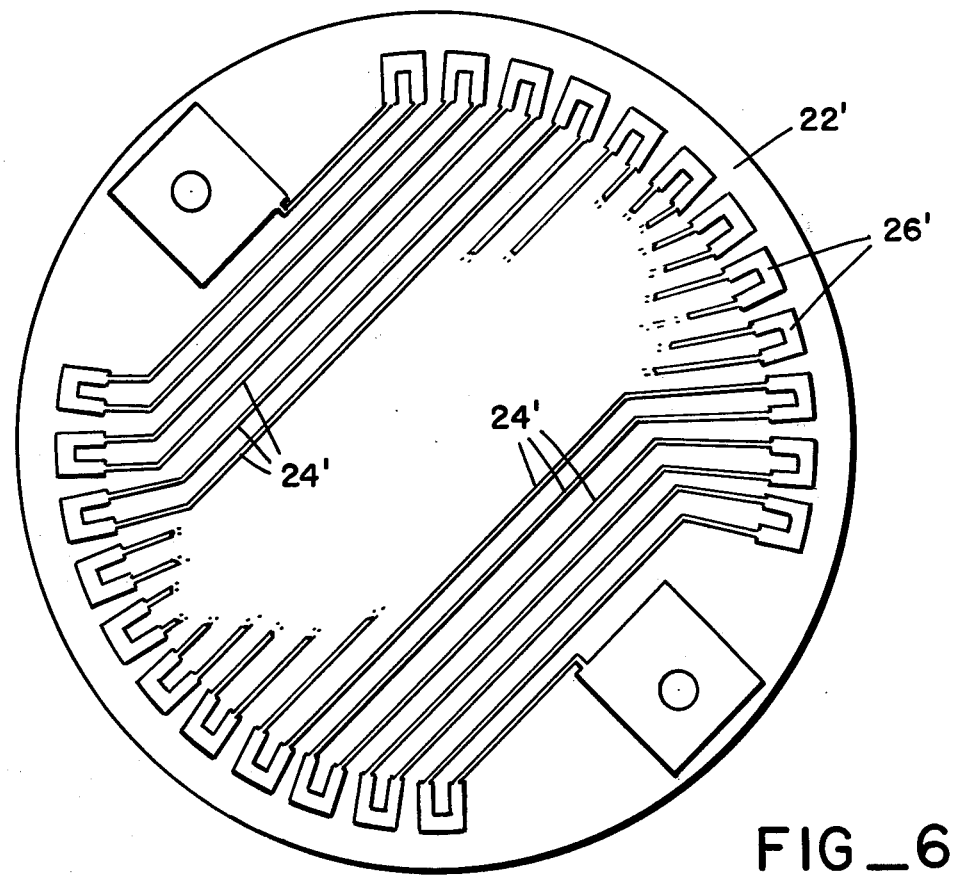
FIG_6

METHOD OF AND APPARATUS FOR DETECTING CONDUCTIVE PARTICLES IN AN OIL FLOW SYSTEM

BACKGROUND OF THE INVENTION

This invention relates to a method of and apparatus for detecting the presence of conductive particles in an oil flow system as, for example, in the lubricating system of internal combustion or jet engines and more particularly to such a method and apparatus adapted to give an indication of the quantity of such conductive particles present.

The presence of metal particles in the lubricating system of internal combustion or jet engines is not only harmful to such engines in operation but an increasing quantity of such particles is indicative of excessive wear of frictional surfaces of such engines. The detection of the presence of such particles and particularly of an increasing quantity of such particles will enable their removal both to prevent damage to the engine and for analysis in order to determine the condition of the engine. Since different frictional surfaces of the engine are made of different metals, it would be possible to detect a defect in a particular part of the engine such as the pistons, cylinders, bearing etc. by analysis of metal particles present in the oil flow of the lubricating system thereof upon detection of an increasing quantity of such particles.

Apparatus for this purpose heretofore proposed in the prior art has been based on the electrical sensing of metal particles as they pass through structures interposed in the oil flow and comprising spaced electrically conductive bodies or electrodes. For example, U.S. Pat. No. 2,349,992 to Schrader discloses various embodiments of such a device in which the presence of metal particles in the oil flow through the volume defined between spaced electrodes results in capacitive or resistive changes that are electrically sensed.

However, the electrodes of such devices must be physically close spaced from each other in order to provide the sensitivity required to detect minute metal particles distributed in the oil flow. The result is that such devices tend to act as fluid filters, collecting both metal particles and non-metallic contaminants. Thus, such devices tend to indicate the presence of an excessive quantity of metal particles, even under normal engine conditions, or to become clogged with non-metallic contaminants.

According to the teaching of U.S. Patent No. 3,457,504 to Arthur et al, an attempt is made to overcome the inherent problem described above by accenting the fluid filter characteristics of the device and decreasing the sensitivity of the electrical elements thereof. However, such an approach only tends to transfer the problem from the electrical elements to the filter element thereof since the relative condition of the filter element at any point in time will tend to determine the operating characteristics of the device. Thus, if the filter is made fine enough to trap the large quantity of minute particles of metal required to produce the desired electrical output, it will also trap a large quantity of non-metallic contaminants, thereby tending to reduce the oil flow therethrough and effectively deactivating the device for the purpose intended.

It is an object of this invention to provide an improved method and apparatus for detecting the presence and quantity of minute metal particles in an oil flow system.

It is another object of this invention to provide an improved method for detecting the presence and quantity of minute metal particles in an oil flow system without the use of fluid filter structures or inherent fluid filter action.

It is yet another object of this invention to provide improved apparatus for use in combination with a resistive type sensor in indicating the presence and quantity of conductive materials in an oil flow system.

It is a further object of this invention to provide an improved sensor element for use in such apparatus, which sensor element is highly sensitive to the presence of minute metal particles in such system but has no inherent fluid filtering characteristics.

SUMMARY OF THE INVENTION

Briefly, according to this invention, the presence and quantity of conductive materials in an oil flow system are sensed by allowing such materials to settle out of the oil at a point in the system where such oil is relatively static onto a generally planar insulating surface having an array of elongated close spaced substantially parallel electrically conductive surface portions thereon. A plurality of discrete electrically resistive elements are electrically connected in series with each other and each junction between a pair of serially connected electrically resistive elements is electrically connected to a different one of the elongated electrically conductive surface portions. Thus, conductive metal particles settling on such planar surface will tend to electrically connect the elongated conductive surface portions, changing the total electrical resistance of the series connected electrically resistive elements and such changes in total resistance is sensed in order to sense the presence of metal particles in the oil flow system. The value of the total resistance sensed will be an inverse function of the quantity of metal particles in the oil flow system thus providing for the sensing of the quantity of metal particles in the system.

BRIEF DESCRIPTION OF THE DRAWING

The foregoing and other objects and features of this invention will be more clearly apparent from a reading of the following detailed description of preferred embodiments in conjunction with the attached drawing wherein:

FIG. 1 is a perspective view of a preferred embodiment of the apparatus of this invention with the sensor shown separately from the remainder of the apparatus which is enclosed in an appropriate housing and with the electrical connections between the sensor and the remainder of the apparatus indicated schematically.

FIG. 2 is a schematic representation of a generalized oil flow system to which this invention is applicable and including a showing of the preferred location of the sensor according to the teaching of this invention.

FIG. 3 is an enlarged cross-sectional view in elevation of the sensor according to the preferred embodiment of this invention shown in FIG. 1.

FIG. 4 is an enlarged top plan view of the electrically active element of the sensor of FIG. 3 showing a preferred arrangement of the electrically conductive surfaces on an insulating disc with the resistive elements and other electrical portions of the apparatus shown in generalized schematic form.

FIG. 5 is a detailed schematic representation of the apparatus according to a preferred embodiment of this invention including a schematic representation of the sensor.

FIG. 6 is an enlarged top plan view showing a preferred structure for the electrically active element of the sensor in which both the conductive surfaces and the resistive elements are provided on a major surface of an insulating disc by printed circuit techniques.

DETAILED DESCRIPTION OF PREFERRED EMBODIMENTS

Referring to FIG. 1, a preferred embodiment of the sensor element 10 according to the teaching of this invention is shown in perspective, with a housing 11 containing the remainder of the apparatus according to this invention also shown in perspective. A schematic representation of the electrical interconnection including a battery 12 between the sensor 10 and remainder of the apparatus contained in the housing 11 is included in FIG. 1.

In actual use, the sensor 10 will be installed in an appropriate place in the oil flow system of an engine or other mechanism in accordance with the teaching of this invention and the housing 11 contaning the remainder of the apparatus will be mounted at a point where it may be conveniently observed by the operator of the engine or other machine. For example, where the teaching of tis invention is applied to an internal combustion engine, the sensor 10 would be mounted in the oil pan of the engine and the housing 11 could be mounted on the dashboard or instrument panel together with the other instruments which monitor the operation of the engine. If a battery is not associated with the engine or other machine to which this invention is applied, then an appropriate battery or other source of DC electrical energy must be provided.

Referring to FIG. 2, the essential elements of an oil flow system to which this invention is applicable are shown in generalized form. Thus, such oil flow system must include a portion such as an oil reservior or oil pan represented at 14 where a quantity of the oil in the system is in a relatively static state. Represented at 16 is a pump or other appropriate means for urging oil to flow from the reservoir 14 to an engine or other machine represented at 18 for the lubrication thereof after which the oil returns to the reservoir 14. According to the teaching of this invention, the sensor 10 is mounted in a wall of the reservoir 14. According to the teaching of this invention, the sensor 10 is mounted in a wall of the reservoir 14 where the force of gravity will cause relatively heavy metal particles to settle out of the relatively static quantity of oil in the reservoir 14 onto the sensor 10. Thus, the sensor 10 is preferably mounted at the point in the reservoir 14 normally occupied by the drain plug provided in the prior art for draining the oil from the oil flow system. However, the sensor 10 may be located at any point in the wall of the reservoir where it will be exposed to the settling of a representative amount of heavy metal particles from the oil by the force of gravity.

Referring to FIG. 3, a preferred embodiment of the sensor 10 according to the teaching of this invention is shown in enlarged cross-section. Such sensor 10 comprises a metallic body 20 in the form of a threaded plug with a hexagonal head, as best shown in FIG. 1, similar to the drain plugs conventionally used in oil flow systems. In fact, according to the preferred embodiment of this invention, the sensor 10 actually comprises the drain plug of the oil flow system suitably modified to include the electrical elements according to the teaching of this invention as will be more fully discussed hereinbelow. In any event, the metallic body 20 serves as the mount for the sensor pill 22 with a major surface thereof exposed to the oil in the reservior or other relatively static point in the oil flow.

Referring to FIG. 4, an enlarged top plan view of the major surface of the sensor pill 22 which is exposed to the oil is shown. Such sensor pill comprises a planar array of a plurality of elongated mutually spaced electrically conductive surfaces 24. According to the preferred embodiment of this invention, such planar array of electrically conductive surfaces 24 are provided on an appropriate insulating substrate such as a mica disc, for example. Such electrically conductive surfaces 24 are preferably made of copper coated with gold in order to provide high electrical conductivity and resistance to corrosion or other chemical effects due to their direct contact with the oil of the oil flow system. Conventional techniques such as the photographic printing and etching techniques conventionally used in making printed circuit boards may be conveniently used in fabricating the sensor pill 22 according to the teaching of this invention.

As shown in FIG. 4, the sensor pill 22 also includes a plurality of electrically resistive elements 26. According to the teaching of this invention, such electrically resistive elements are electrically connected in series with each other across the battery 12 or other source of DC electrical energy through the remaining portion of the apparatus of this invention schematically indicated in FIG. 4 by the ammeter 11 '. According to this invention, the junction between each pair of series connected electrically resistive elements 26 is electrically connected to a different one of the electrically conductive surfaces 24. In fact, in the embodiment shown in FIG. 4, the electrically conductive surfaces 24 each form the junction between a different pair of electrically resistive elements 26. Thus, in operation, a DC electrical current is established by the battery 12 or other source through the apparatus which current flow is essentially determined by the total resistance of the electrically resistive elements 26 and may be indicated by an ammeter such as that represented generally at 11 ' in FIG. 4.

If a metal particle or plurality of metal particles settle onto the sensor pill 22 in such a way as to form an electrically conductive bridge between any pair of electrically conductive surfaces 24, they will tend to establish a low resistance electrical current path therebetween in parallel with one of the electrically resistive elements 26 thereby tending to reduce the total resistance of the apparatus and increase the current flow therethrough. If a large quantity of metal particles are present in the oil, they will tend to settle over the surface of the pill 22 resulting in a large reduction in the total resistance of the apparatus and a large current flow therethrough whereas a lesser number of metal particles will result in a lesser reduction in resistance and a lesser current flow therethrough. Thus a change in the total resistance of the apparatus will indicate the presence of metal particles in the oil and the total value of such resistance will be an inverse function of the quantity of such metal particles.

Referring to FIG. 5, a detailed schematic diagram of a preferred embodiment of the apparatus of this invention is shown in which the sensor element is indicated schematically at 10. Such sensor 10 is connected across the source of DC electrical energy which may be a 12 volt battery, for example, through a current limiting resistor 30, the purpose of which is to reduce the current drain on the DC source. The junction between the sensor 10 and the resistor 30 is connected to the inverting input of an operational amplifier 31 through an input resistor 32. The non-inverting input of the DC amplifier 31 is connected to the adjustable tap of a potentiometer 33 which potentiometer is connected in series with a current limiting resistor 34 and a bias resistor 35 across the source of DC electrical energy. The output of the amplifier 31 is connected to the base of a transistor 36 through an output resistor 37 and across an input resistor 38. The potentiometer 33 is adjusted so that there is no output from the amplifier 31 to cause the transistor 36 to conduct when the resistance of the sensor 10 is at full value. The accumulation of metal particles on the surace of the sensor 10 will reduce the total resistance thereof, thereby reducing the voltage which is developed thereacross and applied to the inverting input of the amplifier 31. This will result in an increased output from such amplifier 31 causing the transistor 36 to conduct in direct proportion to such output. The transistor 36 is connected across the source of DC electrical energy through the solenoid of a milliammeter indicated generally at 40. Thus, as the resistance of the sensor 10 decreases from its normal value to a lower value due to the accumulation of metal particles thereon, the amount of current conducted through the transistor 36 and solenoid 40 of the milliammeter will increase, resulting in a corresponding increase in the reading of the milliammeter from 0.

The output of the amplifier 31 is also connected through a reverse biased zener diode 41 to the base of a second transistor 42. The second transistor 42 is connected in series with a light emitting diode 43 across the source of DC electrical energy through a voltage limiting resistor 44. The transisitor 42 is in a non-conducting condition when there is no output from the amplifier 31 and the resistance of the sensor is at its maximum value. As metal particles accumulate on the sensor 10 reducing the resistance thereof, the voltage output of the amplifier 31 increases until the threshold voltage of the zener diode 41 is reached causing it to conduct and apply the output of the amplifier 31 to the base of transistor 42, thereby allowing current flow through the transistor 42 in proportion to the output of amplifier 31 and tending to cause the light emitting diode to emit light which will increase in intensity as the resistance of the sensor 10 decreases.

As shown in FIG. 1, the light emitting diode 43 may be physically located in close proximity to the scale of the milliammeter 40. Thus, the increasing intensity of the light output of the light emitting didoe 43 will tend to attract the operator's attention to the milliammeter, the reading of which will indicate the quantity of metal particles present on the sensor 10.

Although the apparatus thus far described in connection with FIG. 5 will provide an acceptable level of operation in accordance with the teaching of this invention, we have found that the effectiveness of the apparatus will be greatly increased by periodically pulsing the voltage applied across the sensor 10 to the full voltage value of the source of DC energy. Although the explanation for such improvement in operation due to such pulsing is not fully understood, it is believed that such pulsing results in a more rapid settling of metal particles onto the conductive surfaces of the sensor element 10 and in better electrical contact between such metal particles and such electrically conductive surfaces. In any event, it has been found that the application of a substantially square wave pulse having a pulse width of about one-half second and a repetition rate of about one cycle per second will result in a more efficient electrical contact between the metal particles and the conductive surfaces of the senor element 10. If the repetition rate is increased about 15 pulses per second with a corresponding decrease in pulse width, this effect tends to disappear. Similarly, if the repetition rate is reduced below one pulse every two seconds, no appreciable improvement is noted and the output becomes more difficult to sense with accuracy.

Thus, referring to FIG. 5, in the preferred embodiment of this invention, an appropriate means is included for periodically pulsing the voltage across the sensor element 10 up to the full value of the voltage of the source of DC energy. Such means comprises an operational amplifier 45 together with its associated circuitry. Thus, the source of DC energy is connected to the inverting input of the operational amplifier 45 through a capacitor 46 and a resistor 47 is connected between the inverting input and the output of the amplifier 45. A feed back resistor 48 is connected between the output of the amplifier and the non-inverting input thereof and the non-inverting input of the amplifier 45 is connected to ground through a bias resistor 49. The output of the amplifier 45 is also connected to the junction between the resistor 30 and sensor 10 through an isolating diode 50.

It will be understood that the power supply for the amplifiers 31 and 45 is the source of DC energy although the power supply connections to the amplifiers 31 and 45 are not shown in FIG. 5 for simplicity of illustration. In any event, the capacitor 46 and resistor 47 cooperate to form an RC network and periodically pulse the output of the amplifier 45 to the full voltage value of the source of DC energy with the repetition rate and pulse width being a function of the relative values of the capacitor 46 and resistor 47. It would, of course, be possible to use other appropriate circuits or circuit arrangements for pulsing the voltage across the sensor 10 in accordance with the teaching of this invention.

An additional advantage of pulsing the voltage across the sensor element 10 is that a corresponding pulse will appear in the output of the amplifier 31 which may be used to cause the light emitting diode 43 to flash rather than glow steadily. Thus, as conductive metal particles accumulate on the sensor 10, the light emitting diode 43 will flash with ever increasing brightness. A capacitor 51 is connected across the solenoid of the milliammeter 40. Such capacitor has a large value by comparison to the capacitor 46 of the pulsing circuit thus reducing the excursions of the milliammeter 40 in response to the pulses in the output of the amplifier 31. However, in accordance with the teaching of this invention, the value of the capacitor 51 should not be so large as to completely damp the pulses in the output of the amplifier 31 since a slight pulsation of the milliammeter 40 serves as an indication that the sensor 10 is connected in the circuit and operating properly even though there are not sufficient metal particles present thereon to produce a light output from the light emitting diode 43. Thus, the apparatus shown in FIG. 5 is self-checking at least insofar as indicating proper operation of the sensor element 10 assuming that the remainder of the apparatus is operating properly.

In order to test the remainder of the apparatus shown in FIG. 5, a normally open test switch 52 is connected in parallel with the sensor element 10. Upon closure, the test switch 52 will short out the sensor element and will produce a maximum response from the remainder of the apparatus if it is working properly.

In a preferred embodiment of this invention as actually built and tested, a voltage controlled variable output audio oscillator 60 including speaker 62 was connected in parallel with the light emitting diode 43 as indicated at the terminal 53 connected between the junction of the transistor 42 and the resistor 44. Thus, both a visual and an audio output was provided to attract the attention of the operator to the reading of the milliammeter 40.

In such actual embodiment of the apparatus according to this invention, the sensor element 10 has a total resistance of between 16 and 19 K ohms. The amplifiers 31 and 45 were the two halves of a dual operational amplifier sold by Signetics Corporation under the type number 5558. A feed-back resistor 54 was connected between the output of the amplifier 31 and the inverting input thereof in order to establish a selected amplification level for such amplifier. The elements of the apparatus shown in FIG. 5 as actually built and successfully tested were of the values or types shown in the following table:

| | |
|---|---|
| Resistor 30 | 120 K ohms |
| Resistor 32 | 1 K ohm |
| Resistor 33 | 20 K ohms |
| Resistor 34 | 120 K ohms |
| Resistor 35 | 15 K ohms |
| Transistor 36 | Type No. 2N4400 sold by Motorola, Inc. |
| Resistor 37 | 10 K ohms |
| Resistor 38 | 10 K ohms |
| Milliammeter 40 | 0 to 1 milliamp. |
| Zener diode 41 | Type No. IN4731A sold by Motorola, Inc. |
| Transistor 42 | Type No. 2N4400 sold by Motorola, Inc. |
| Light emitting diode 43 | Type No. MU5053 sold by Monsanto, Inc. |
| Resistor 44 | 270 ohms |
| Capacitor 46 | .1 microfarads |
| Resistor 47 | 120 K ohms |
| Resistor 48 | 120 K ohms |
| Resistor 49 | 12 megohms |
| Diode 50 | Type No. IN34A sold by National Semiconductor, Inc. |
| Capacitor 51 | 100 microfarads |
| Resistor 54 | 470 K ohms |

Referring to FIG. 6, an enlarged plan view of the preferred embodiment 22' of the sensor pill according to this invention is shown. Such sensor pill comprises an epoxy resin substrate upon which 23 equally spaced elongated parallel conductive surfaces 24' of gold clad copper are formed by photoetching techniques. Each conductive 24' is 0.0035 inches (0.01 cm) thick and has a width of between about 0.005 inch (0.0125 cm) and 0.007 inch (0.015 cm). The spacing between the conductive surfaces 24' is between about .00375 inch (0.01 cm) and about 0.005 inch (.0125 cm).

The resistive elements 26' are also formed on the substrate by photoetching techniques by a proprietary process and of a proprietary material having a resistance of about 100 ohms per square. As shown in FIG. 6, each of the resistive elements 26' bridges between the adjacent ends of the different pair of conductive surfaces 24' and is generally U-shaped in order to provide a total resistance of about 700 ohms per resistive element. Since all of the resistive elements 26' are connected in series through the conductive surfaces 24', the total resistance of the sensor pill is between about 16 K and about 19 K ohms. The resistive elements 26' are covered with a coating of epoxy resin type resist material in order to avoid the possibility of any change in resistance thereof due to exposure to the oil of the oil flow system.

In the actual embodiment shown in FIG. 6, the diameter of the pill 22' was about ½ inch (1.27 cm). Theoretically, the sensor pill 22 could have any appropriate shape and dimensions. However, it has been found that operational considerations impose a maximum limitation on dimensions for practical reasons and that a circular shape is preferred as will be discussed hereinafter.

The spacing between the conductive surfaces 24 of the sensor pill 22 is, of course, related to the minimum size metal particle which could be detected according to the teaching of this invention. It has been found that a spacing of about 0.005 inch (.0127 cm) between the conductive surfaces 24 is suitable for detecting metal particles in the lubricating oil flow of truck and diesel engines. For light aircraft and jet engines, a somewhat closer spacing such as 0.00375 inch (.001 cm), for example, is preferred. However, although the sensor pill 22 must be capable of sensing minute particles comparable to such spacings, it is important that the apparatus according to this invention not be so sensitive as to give a warning indication when there are only a few of such minute metal particles in the oil flow. The sensitivity of the apparatus to the number of metal particles present in the oil flow is a function of both the number of conductive surfaces and the width of such surfaces.

Thus, it has been found that the width of the conductive surfaces may be made at least equal to and preferably somewhat greater than the spacing between the conductive surfaces for ease of manufacture without adversely affecting the sensitivity of the apparatus to the number of metal particles present in the oil flow. In view of the fact that such conductive surfaces are gold clad in order to reduce the formation of highly resistive oxides thereon due to contact with the oil, it is desirable that such surfaces not be made too large.

It has also been found that if too few conductive surfaces are used, the apparatus will be too sensitive to the number of metal particles present and will give a warning indication when in fact there is no need for concern. If too many conductive surfaces are used, then the device will not be sensitive enough to the number of metal particles present in the oil flow to give a warning indication in time to avoid damage to the engine. It has been found that at least 15 but not more than 30 conductive surfaces will give satisfactory results where the maximum length of such conductive surfaces is about 100 times the spacing between such conductive surfaces (i.e., about .5 inch (1.25 cm). It will be understood that the probability of a metal particle bridging the spacing between a particular pair of conductive surfaces and thus the sensitivity of the sensor pill to the number of metal particles present in the oil flow will increase in direct proportion to the maximum length of the conductive surfaces. Thus, as the length of the conductive surfaces is increased, the number of conductive surfaces must also be increased in order to avoid the possibility that the apparatus will give false warnings as to the quantity of metal particles present in the oil flow. Again, the expense of the gold clad conductive surfaces imposes a practical limitation on the length and number of conductive surfaces used in the sensor pill.

It has been found that a sensor pill of appropriate dimensions can be made to fit into the drain plug of the oil systems of the various engines in use today. Thus, referring to FIGS. 1 and 3, it will be seen that it is a simple matter to drill an appropriate centrally located aperture through a drain plug for the installation of a sensor pill 22 and appropriate insulated electrical connections 21 and 23 therein. If the drain plug 20 is not already provided with a cup-like recess in its extremity as illustrated in FIG. 3, then it is preferably provided with such a recess having a depth indicated by the arrow B which is at least one-fourth of the diameter thereof indicated by the arrow A. The sensor pill 22 may be mounted in the bottom of such recess through the use of an appropriate epoxy resin and an appropriate fillet of epoxy resin is preferably provided about the upper periphery of the sensor pill 22 to direct metal particles onto the electrically active surface as they settle into such recess.

It has been found that 90% of all diesel engines in use today utilize one of four different drain plugs. Similarly it has been found that 90% of all light aircraft engines and 90% of all jet engines utilize on of not more than three different drain plugs and it is estimated that 90% of the automobiles in use today utilize one of not more than five different drain plugs.

Furthermore, it has been found that a sensor pill comprising a circular disc about one-half inch in diameter can be easily mounted in any one of the widely used drain plugs mentioned above. Thus, according to the teaching of this invention, it is proposed to make sensor pills in two sizes, namely, 0.550 inch (1.4 cm) for use in connection with diesel engines and 0.405 inch (1 cm) for use in connection with light aircraft engines, jet engines and automobiles.

Although the use of apparatus according to the teaching of this invention for sensing the presence and quantity of conductive metal particles in oil flow has been emphasized hereinabove, it will be understood that the apparatus of this invention is capable of sensing the presence of any conductive material in oil flow which has a specific gravity greater than the oil. Thus, the presence of water in the oil flow can be sensed by the apparatus of this invention and in fact, there will be a tendency for moisture to settle on the sensor pill whenever an engine remains idle for an extended period of time under conditions which would promote the condensation of moisture within the oil system. In marine applications for diesel engines, it would be highly desirable to sense the presence of salt water, for example, in the oil flow system. However, in most applications the moisture will tend to evaporate from the oil when it is heated, due to the operation of the engine. Thus it is to be expected that the apparatus of this invention will often give a warning indication after an engine to which it is applied has remained idle for an extended period of time. The length of time required to evaporate the moisture from the sensor pill in operation may give some indication of the quantity of water present in the oil flow and thus could be expected to provide some indication as to the source of the water and the severity of the condition.

It is also to be expected that nonconductive contaminants will tend to accumulate on the sensor pill. For example, in gasoline engines, a sludge comprised of tetraethyl lead will tend to build up on the sensor pill. However, such sludge will be removed whenever the drain plug is removed in order to change the engine oil. Thus, a build-up of nonconductive contaminants on the pill will tend to be prevented by the normal maintenance procedures followed in connection with all engines.

It is believed that those skilled in the art will make obvious modifications and changes in the specific embodiments described hereinabove and shown in the attached drawings in order to adapt the apparatus for specific applications. In particular, the specific dimensions mentioned hereinabove subject to the limitations as specifically described may be changed and it is anticipated that various electrical circuitry could be used to provide the necessary audio and visual warnings or readings to indicate the presence of conductive materials in the oil flow system.

What is claimed is:

1. The method of sensing the presence and quantity of conductive materials in a flow system for high electrical resistance fluid comprising the steps of:
   a. positioning an electrically insulating substrate having a major surface with a plurality of elongated close spaced substantially parallel electrically conductive surfaces thereon below the normal level of fluid at a point in said system where the fluid flow is relatively static whereby conductive materials having a higher specific gravity than said fluid may contact said major surface of said substrate;
   b. electrically connecting each of said elongated conductive surfaces at the junction between a different pair of a plurality of series connected electrical resistance elements providing a given total electrical resistance;
   c. electrically isolating said plurality of series connected electrical resistance elements from said fluid of said flow system;
   d. passing a given electrical current flow through said series connected electrical resistance elements; and
   e. sensing effective decreases in said given total electrical resistance due to conductive materials which contact said substrate in a position to bridge the space between adjacent ones of said elongated close spaced substantially parallel conductive surfaces thereon.

2. The method of claim 1 including the step of pulsing said electrical current flow through said series connected electrical resistance elements.

3. The method of claim 2 including the step of generating a visual output signal which increases in direct proportion to said effective decreases in said given total electrical resistance of said series connected electrical resistance elements.

4. The method of claim 2 including the step of generating an audio output signal which increases in direct proportion to said effective decreases in said given total electrical resistance of said series connected electrical resistance elements.

5. The method of claim 2 including the step of recessing said insulating substrate in a substantially horizontal wall of said fluid flow system by a distance at least equal to one quarter of the maximum surface dimension of said insulating substrate.

6. The method of claim 2 including the step of pulsing said electrical current flow through said series connected electrical resistance elements from a given DC value to a higher DC value at a repetition rate between one-half pulse per second and 15 pulses per second.

7. Apparatus for sensing the presence and quantity of conductive materials in a flow system for high electrical resistance fluid comprising:
   a. an insulating substrate having a major surface with a plurality of elongated close spaced substantially parallel electrically conductive surfaces thereon positioned within said fluid flow system below the normal level of fluid at a point in said system where said fluid flow is relatively static whereby conductive materials having a higher specific gravity than said fluid may contact said major surface of said substrate;
   b. a plurality of electrical resistance elements electrically connected in series to provide a given total electrical resistance with the junction between each pair of said plurality of electrical resistance elements comprising a different one of said plurality of elongated close spaced substantially parallel electrically conductive surfaces on said one major surface of said electrically insulating substrate;
   c. means electrically isolating said plurality of electrical resistance elements from said fluid of said flow system;
   d. means for passing a given electrical current flow through said series connected electrical resistance elements; and
   e. means for sensing and indicating the effective decreases in said given total electrical resistance of said series connected electrical resistance elements due to conductive materials which contact said major surface of said substrate in a position to bridge the space between adjacent ones of said elongated close spaced substantially parallel conductive surfaces thereon.

8. Apparatus as claimed in claim 7 including means for pulsing said given electrical current flow through said series connected electrical resistance elements.

9. Apparatus as claimed in claim 7 including means for providing a visual output signal which increases in a direct proportion to said effective decreases in said total electrical resistance of said series connected electrical resistance elements.

10. Apparatus as claimed in claim 7 wherein said insulating substrate is mounted in a recess in generally horizontal wall of said fluid flow system, said recess having a depth at least equal to one quarter of the maximum transverse dimension thereof.

11. Apparatus as claimed in claim 7 wherein said means for sensing and indicating effective decreases in said given total electrical resistance includes means for inverting and amplifying the voltage developed across said series connected electrical resistance elements by said electrical current flow therethrough, electrical current responsive visual output means, and means for establishing an electrical current flow through said electrical current responsive visual output means which varies in a direct proportion to said inverted and amplified voltage.

12. Apparatus as claimed in claim 11 wherein said electrical current responsive visual output means comprises an ammeter.

13. Apparatus as claimed in claim 11 wherein said electrical current responsive visual means comprises a light emitting diode.

14. Apparatus as claimed in claim 8 wherein said means for pulsing said given electrical current flow through said series connected electrical resistance elements comprises a solid state operational amplifier electrically connected to provide a substantially square wave DC currect output to said series connected electrical resistance elements.

15. A sensor for use in apparatus for sensing conductive particles in a flow system for high electrical resistance fluid, said sensor comprising:
   a. an insulating body having a planar surface;
   b. an array of a plurality of elongated close spaced generally parallel electrically conductive surfaces mounted on said planar surface of said insulating body;
   c. a plurality of electrical resistance elements each electrically connected between a different pair of said plurality of elongated close spaced generally parallel electrically conductive surfaces;
   d. protective means isolating said plurality of electrical resistance elements from their environment; and
   e. means for making electrical connections to the ultimate one of said plurality of conductive surfaces at each side of said array of said plurality of conductive surfaces.

16. A sensor for use in apparatus for sensing conductive particles in a fluid flow system as claimed in claim 15 wherein each conductive surface of said array of said conductive surfaces is spaced from an adjacent conductive surface of said array a distance less than about .005 inch (.0127 cm), the maximum length of said conductive surfaces of said array of conductive surfaces is about 100 times said distance by which each of said conductive surfaces of said array is spaced from an adjacent conductive surface and said array includes at least 15 but not more than 30 conductive surfaces.

17. A sensor for use in apparatus for sensing conductive particles in a fluid flow system as claimed in claim 15 wherein each of said plurality of electrical resistance elements comprises a discrete coating of electrically resistive material deposited on said planar surface of said insulating body and said protective means comprises insulating coatings covering each of said plurality of electrical resistance elements.

18. A sensor as claimed in claim 15 for use in apparatus for sensing conductive particles in an oil flow system wherein said insulating body comprises a circular disc having a major surface of about one-half inch (1.27 cm) in diameter.

19. A sensor for use in apparatus for sensing conductive metal particles in an oil flow system as claimed in claim 18 wherein said insulating body is mounted in a circular recess in the inner end of the drain plug of the oil flow system with said array of conductive surfaces on said insulating body exposed to the oil in said oil flow system.

20. A sensor for use in apparatus for sensing conductive metal particles in an oil flow system as claimed in claim 19 wherein said array of conductive surfaces includes at least 15 and not more than 30 conductive surfaces deposited on said disc, said electrical resistance elements comprise coatings of electrically resistive material deposited on said disc at opposite ends of said conductive surfaces, and said protective means comprises coatings of insulating material covering coatings of electrically resistive material.

* * * * *

UNITED STATES PATENT OFFICE
CERTIFICATE OF CORRECTION

Patent No. 4,030,028           Dated June 14, 1977

Inventor(s) DAVID G. ALLENDER

It is certified that error appears in the above-identified patent and that said Letters Patent are hereby corrected as shown below:

```
Column 3, line 40    - Change "reservior" to --reservoir--.
Column 3, lines 46-48 - Delete the repetitive "According
                       to the teaching of this invention,
                       the sensor 10 is mounted in a wall of the
                       reservoir 14."
Column 7, line 57    - After "conductive" insert --surface--.
Column 7, line 67    - Change "the" second occurrence to -- a --.
Column 9, line 15    - Before "extremity" insert --inner--.
Column 9, line 29    - Change "on" to --one--.
Column 11,line 51    - Before "generally" insert --a--.
Column 12,line 66    - After "covering" insert --said--.
```

Signed and Sealed this

First Day of May 1979

[SEAL]

Attest:

RUTH C. MASON
Attesting Officer

DONALD W. BANNER
Commissioner of Patents and Trademarks